United States Patent [19]

Patil

[11] Patent Number: 5,399,277
[45] Date of Patent: Mar. 21, 1995

[54] FUEL AND LUBRICANT ADDITIVES DERIVED FROM DIHYDROXYAROMATIC COMPOUNDS

[75] Inventor: Abhimanyu O. Patil, Westfield, N.J.

[73] Assignee: Exxon Chemical Patents Inc., Linden, N.J.

[21] Appl. No.: 134,246

[22] Filed: Oct. 8, 1993

[51] Int. Cl.⁶ .................... C10M 149/00; C10L 1/22
[52] U.S. Cl. .................... 252/51.5 R; 44/426; 44/427; 44/428; 564/339; 564/395; 564/403
[58] Field of Search ............... 564/395, 403; 44/426, 44/427, 428; 252/51.5 R

[56] References Cited

U.S. PATENT DOCUMENTS

| 3,214,472 | 10/1965 | Charle et al. | 564/403 |
| 3,965,182 | 6/1976 | Worrel | 564/403 |
| 4,708,809 | 11/1987 | Davis | 252/51.5 R |
| 4,740,321 | 4/1988 | Davis et al. | 252/51.5 R |
| 5,028,394 | 7/1991 | Lowell, Jr. et al. | 422/58 |
| 5,113,018 | 5/1992 | Kurano et al. | 564/403 |

FOREIGN PATENT DOCUMENTS 1104522  4/1959  Germany ................. 564/403

Primary Examiner—Ellen M. McAvoy
Attorney, Agent, or Firm—Ken R. Walton

[57] ABSTRACT

The present invention relates to a novel process for the production of fuel and lubricant additives useful as dispersants and multifunctional viscosity modifiers wherein a dihydroxyaromatic compound is alkylated with an olefinic polymer and then aminated in such a manner as to oxidize the hydroxyl moieties of the dihydroxyaromatic compound to carbonyl groups.

20 Claims, No Drawings

FUEL AND LUBRICANT ADDITIVES DERIVED FROM DIHYDROXYAROMATIC COMPOUNDS

FIELD OF THE INVENTION

The present invention relates to a novel process for producing fuel and lubricant additives such as dispersants, viscosity modifiers, and multifunctional viscosity modifiers by alkylating and then aminating dihydroxyaromatic compounds, such as catechol and hydroquinone.

BACKGROUND OF THE INVENTION

Liston et al., U.S. Pat. Nos. 4,632,771 and 4,643,838 for NORMALLY LIQUID $C_{18}$ TO $C_{24}$ MONOALKYL CATECHOLS refer to normally liquid lubricating oil additives which provide both antioxidant and friction-modifying properties when added to lubricating oil. In particular, these patents relate to $C_{18}$ to $C_{24}$ alkyl catechol lubricating oil additives which are normally liquid at typical storage temperatures.

Werner et al., U.S. Pat. No. 4,265,833 for a PROCESS FOR THE PREPARATION OF HYDROXY-DIPHENYLAMINES refers to a process for the preparation of hydroxy-diphenylamines by condensation of dihydroxybenzene with an excess amount of primary aromatic amine in the presence of a catalytic amount of an acid at elevated temperature, wherein the excess aromatic amine and the reaction product is distilled off from the reaction mixture in the presence of a base.

Coupland et al., U.S. Pat. No. 3,592,820 for SUBSTITUTED CATECHOL SALTS OF BENZOTRIAZOLES OR PHENYLHYDRAZINES refers to a compound which may be produced by reaction of substituted catechol with phenylhydrazine, substituted phenylhydrazine, benzotriazole, or substituted benzotriazole. The reaction may be carried out in an inert solvent, such as a hydrocarbon. The compounds are useful as antioxidants in lubricant compositions.

Small, Jr. et al., U.S. Pat. No. 5,061,390 for DIETHYLAMINE COMPLEXES OF BORATED ALKYL CATECHOLS AND LUBRICATING OIL COMPOSITIONS CONTAINING THE SAME refers to lubricating oils containing a borated alkyl catecholdiethylamine complex effective in reducing oxidation, wear, and deposits in internal combustion engines.

Davis, U.S. Pat. No. 4,663,063 for ALKYL PHENOL AND AMINO COMPOUND COMPOSITIONS AND TWO-CYCLE ENGINE OILS AND FUELS CONTAINING SAME refers to a composition comprising the combination of (A) at least one alkyl phenol of the formula $(R)_a$—Ar—$(OH)_b$ wherein each R is independently a substantially saturated hydrocarbon-based group of an average of at least about 10 aliphatic carbon atoms; a and b are each independently an integer of one up to three times the number of aromatic nuclei present in Ar with the proviso that the sum of a, b, and c does not exceed the unsatisfied valences of Ar; and Ar is an aromatic moiety which is a single ring, a fused ring or a linked polynuclear ring having 0 to 3 optional substituents selected from the group consisting essentially of lower alkyl, lower alkoxyl, carboalkoxy methylol or lower hydrocarbon-based substituted methylol, nitro, nitroso, halo and combinations of said optional substituents, and (B) at least one amino compound with the proviso that the amino compound is not an amino phenol. Lubricants and lubricating oil-fuel mixtures for two-cycle engines which include the above compositions, and methods for lubricating two-cycle engines are also disclosed.

When a polymer chain is functionalized with a hydroxyaromatic, it is well known in the art to derivatize the alkylated hydroxyaromatic with an amine in the presence of an aldehyde. This derivatization is known as a Mannich Base reaction. In the present invention, dihydroxyaromatics may be derivatized with amines without the use of an aldehyde—thereby saving the expense of utilizing a reagent that is consumed in the reaction.

SUMMARY OF THE INVENTION

In the present invention, a dihydroxyaromatic compound is alkylated with a polymer alkylating agent and then reacted with an amine under reaction conditions effective in oxidizing the hydroxyl groups to carbonyl groups. The preferred dihydroxyaromatic compounds are catechol and hydroquinone.

The products of the present invention demonstrate highly effective sludge and varnish reducing properties when used as fuel and lubricant dispersant additives.

DETAILED DESCRIPTION OF THE INVENTION

The process of the present invention may be described by the following illustrative formulas wherein catechol, for example, is first alkylated and then aminated with an amine:

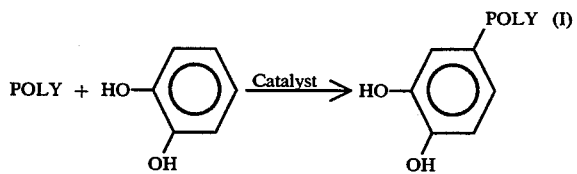

followed by:

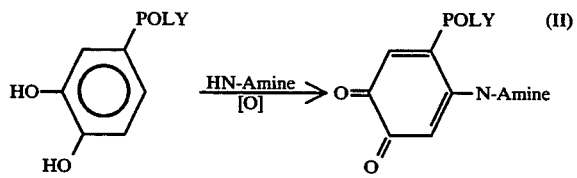

wherein [O] indicates oxidation; POLY represents a polymer alkylating agent which will react with the aromatic ring so as to attach as a polymeric hydrocarbyl moiety (i.e., -POLY) thereto; and wherein HN-Amine symbolizes a primary or secondary amine and the particular nitrogen moiety thereof that takes part in the amination reaction; and wherein —N-Amine symbolizes the amine bonded directly to the ring via the reacting nitrogen atom as a result of the amination reaction.

Similarly, the final reaction product of the present invention wherein hydroquinone is utilized may be represented by, for example, the following formula:

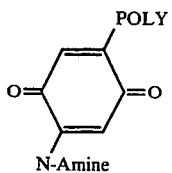

though it is not required that the N-Amine and POLY moieties be diametrically opposed as shown.

The reaction is unusual in that, unlike a Mannich Base reaction, no formaldehyde is needed. Also unlike a Mannich Base is that the hydroxyl groups are oxidized to carbonyl groups, the ring loses its aromaticity, and the nitrogen atom bonds directly with the ring.

The resulting compositions are very effective as a dispersant in reducing oil sludge and varnish in internal combustion engines.

The Dihydroxyaromatic Compounds

Dihydroxyaromatic compounds useful in the present invention include, but are not limited to, hydroquinone, catechol, hydrocarbyl-substituted dihydroxyaromatics such as methyl hydroquinone, ethylhydroquinone, 2-phenylhydroquinone, chlorohydroquinone, 3-methylcatechol, 4-methylcatechol, and the like. Also useful are dihydroxynapthols such as 1,4-dihydroxynaphthalene, 1,2-dihydroxynaphthalene and the like.

Dihydroxyaromatics useful in the present invention include those represented by the following formulas:

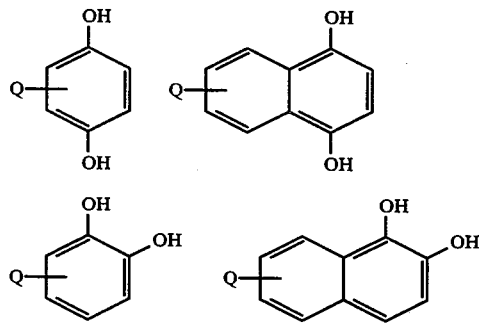

wherein Q is a substituent comprising a halide radical, an aryl group, hydrogen, a hydrocarbyl having 1 to 12 carbon atoms, or a structure of the form:

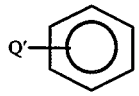

and wherein Q' is defined as Q above, the same or different, and wherein one or more sides may be shared with the moiety so substituted.

For the purposes of this invention, the term "hydrocarbyl" is not strictly limited to moieties possessing solely carbon and hydrogen, but rather may encompass a minor degree of substitution so long as the processes and benefits of the invention are not thwarted thereby.

The Polymer Alkylating Agents

Polymer alkylating agents which are useful in the present invention are polymers containing at least one carbon-carbon double bond unsaturation (olefinic, or "ethylenic") and which are not so sterically hindered, or in reactive competition with other functional groups, so as to render them unable to participate in the catalytic alkylation of the chosen dihydroxyaromatic compound. As long as a chosen double bond will react in the presence of a chosen catalyst so as to alkylate a chosen dihydroxyaromatic compound, such a bond will be deemed a "reactive" unsaturation and the polymer possessing such an unsaturation will be deemed a polymer alkylating agent.

Useful polymer alkylating agents in the present invention include polyalkenes including homopolymer, copolymer (used interchangeably with interpolymer) and mixtures thereof. Homopolymers and interpolymers include those derived from polymerizable olefin monomers of 2 to about 16 carbon atoms; usually 2 to about 6 carbon atoms. The interpolymers are those in which two or more olefin monomers are interpolymerized according to well-known conventional procedures to form polyalkenes having units within their structure derived from each of said two or more olefin monomers. Thus, "interpolymer(s)" as used herein is inclusive of terpolymers, tetrapolymers, and the like. As will be apparent to those of ordinary skill in the art, the polyalkenes from which the poly-substituent of Formulas I and II are derived are often conventionally referred to as "polyolefin(s)".

Useful polymers include those described in U.S. Pat. Nos. 4,234,435, 5,017,299, 5,186,851 and European Patent Application No. 0,462,319-A1. Particular reference is made to the α-olefin polymers to be made using organometallic coordination compounds as disclosed therein. A particularly preferred class of polymers are ethylene/α-olefin copolymers such as those disclosed in U.S. Pat. No. 5,017,299 and 5,186,851.

The preferred polymer alkylating agents for use in this invention possess at least one carbon-carbon unsaturated double bond. The unsaturation can be terminal, internal, or both. Preferred polymers have terminal unsaturation. The polymers of the present invention preferably comprise a high degree of terminal unsaturation. For the purposes of this invention, "terminal unsaturation" refers to the unsaturation provided by the last monomer unit located in the polymer. The unsaturation can be located anywhere in this terminal monomer unit. Terminal olefinic groups include ethenylidene (also known as "vinylidene") unsaturation, $R^aR^bC=CH_2$; trisubstituted olefin unsaturation, $R^aR^bC=CR^cH$; vinyl unsaturation, $R^aHC=CH_2$; 1,2-disubstituted terminal unsaturation, $R^aHC=CHR^b$; and tetra-substituted terminal unsaturation, $R^aR^bC=CR^cR^d$. At least one of $R^a$ and $R^b$ is a polymeric group, and the remainder are hydrocarbyl groups, polymeric or otherwise, the same or different.

Especially preferred polymers for use in this invention exhibit substantial terminal ethenylidene unsaturation. At least about 30%, preferably at least about 50%, more preferably at least about 60%, and most preferably at least about 75% (e.g., 75 to 98%), of such polymer chains exhibit terminal ethenylidene unsaturation. Such polymers also may exhibit a minor percentage of highly desirable ethenyl(vinyl) unsaturation, which may be substituted for ethenylidene unsaturation in arriving at the percentages disclosed above. Hence, for example, a combined percentage of 30% ethenylidene and ethenyl unsaturation will more than adequately substitute for 30% ethenylidene alone—and should even prove superior by virtue of the higher reactivity of terminal ethenyl in comparison to that of terminal ethenylidene.

The homopolymers and copolymers of the present invention can be conveniently characterized based on molecular weight range. Polymers and copolymers of "low", "intermediate" and "high" molecular weights can be prepared.

Low molecular weight polymers, also referred to herein as "dispersant-range" molecular weight polymers, are considered to be polymers having a number average molecular weight of less than 20,000 (e.g., about 250 to about 20,000; preferably from at least 400 to about 20,000 (e.g., 450 to 1000; 500 to 2000; 700 to 3000; 1,000 to 19,000); more preferably from about 1,500 to about 10,000 (e.g., 2,000 to 8,000); and most preferably from 1,500 to 5,000. The low molecular weights are number average molecular weights measured by vapor phase osmometry or gel permeation chromatography (GPC). Low molecular weight polymers are useful in the present invention for forming dispersants for fuel and lubricant additives.

Medium molecular weight polymers, also referred to herein as "viscosity-modifier-range" molecular weight polymers, have number average molecular weights ranging from 20,000 to 200,000; preferably 25,000 to 100,000; and more preferably from 25,000 to 80,000 and are useful in the present invention for making viscosity index improvers for lubricating oil compositions, fuels, adhesive coatings, tackifiers and sealants. The medium number average molecular weights can be determined by membrane osmometry.

The high molecular weight materials have a number average molecular weights of greater than about 200,000 and can range from 201,000 to 15,000,000; a specific embodiment of 300,000 to 10,000,000; and more specifically 500,000 to 2,000,000. These polymers are useful in polymeric compositions and blends including elastomeric compositions. Higher molecular weight materials having number average molecular weights of from 20,000 to 15,000,000 can be measured by gel permeation chromatography with universal calibration, or by light scattering as recited in Billmeyer, Textbook of Polymer Science, Second Edition, pp. 81–84 (1971).

The values of the ratio Mw/Mn, also referred to as molecular weight distribution, (MWD) are not critical. However, a typical minimum Mw/Mn value of about 1.1 to 2.0 is preferred with typical ranges of about 1.1 up to about 4.

Useful olefin monomers from which the polyalkenes can be derived are polymerizable olefin monomers characterized by the presence of one or more unsaturated double bonds (i.e., $>C=C<$); that is, they are monoolefinic monomers such as ethylene, propylene, butene-1, isobutylene, and octene-1 or polyolefinic monomers (usually diolefinic monomers) such as butadiene-1,3 and isoprene.

These olefin monomers are preferably polymerizable terminal olefins; that is, they possess terminal unsaturation. However, polymerizable internal olefin monomers (sometimes referred to as medial olefins) characterized by the presence within their structure of the moiety:

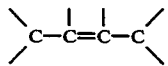

can also be used to form the polyalkenes. When internal olefin monomers are employed, they normally will be employed with terminal olefins to produce polyalkenes which are interpolymers. For purposes of this invention, when a particular polymerized olefin monomer can be classified as both a terminal olefin and an internal olefin, it will be deemed to be a terminal olefin. Thus, for example, pentadiene-1,3 (i.e., piperylene) is deemed to be a terminal olefin for purposes of this invention.

While the polyalkenes generally are hydrocarbon polyalkenes, they can contain substituted hydrocarbon groups such as lower alkoxy, lower alkyl mercapto, hydroxyl, mercapto, and carbonyl, provided the non-hydrocarbon moieties do not substantially interfere with the functionalization reactions of this invention. Preferably, such substituted hydrocarbon groups normally will not contribute more than about 10% by weight of the total weight of the polyalkenes. Since the polyalkene can contain such non-hydrocarbon substituent, it is apparent that the olefin monomers from which the polyalkenes are made can also contain such substituents. Normally, however, as a matter of practicality and expense, the olefin monomers and the polyalkenes will be free from non-hydrocarbon groups. (As used herein, the term "lower" when used with a chemical group such as in "lower alkyl" or "lower alkoxy" is intended to describe groups having up to seven carbon atoms.)

Although the polyalkenes may include aromatic groups—particularly phenyl groups and lower alkyl- —and/or lower alkoxy-substituted phenyl groups such as para-(tertbutyl)phenyl—and cycloaliphatic groups, such as would be obtained from polymerizable cyclic olefins or cycloaliphatic substituted-polymerizable acrylic olefins, the polyalkenes usually will be free from such groups. Again, because aromatic and cycloaliphatic groups can be present, the olefin monomers from which the polyalkenes are prepared can contain aromatic and cycloaliphatic groups.

There is a general preference for polyalkenes which are derived from the group consisting of homopolymers and interpolymers of terminal hydrocarbon olefins of 2 to about 16 carbon atoms. A more preferred class of polyalkenes are those selected from the group consisting of homopolymers and interpolymers of terminal olefins of 2 to about 6 carbon atoms, more preferably 2 to 4 carbon atoms.

Specific examples of terminal and internal olefin monomers which can be used to prepare the polyalkenes according to conventional, well-known polymerization techniques include ethylene; propylene; butene-1; butene-2; isobutylene; pentene-1; hexene-1; heptene-1; octene-1; nonene-1; decene-1; pentene-2; propylene-tetramer; diisobutylene; isobutylene trimer; butadiene-1,2; butadiene-1,3; pentadiene-1,2; pentadiene-1,3; pentadiene-1,4; isoprene; hexadiene-1,5; 2-chloro-butadiene-1,2; 2-methyl-heptene-1; 3-cyclohexylbutene-1; 2-methyl-5-propyl-hexene-1; pentene-3; octene-4; 3,3-dimethyl-pentene-1; styrene; 2,4-dichlorostyrene; divinylbenzene; vinyl acetate; allyl alcohol; 1-methyl-vinyl acetate; acrylonitrile; ethyl acrylate; methyl methacrylate; ethyl vinyl ether; and methyl vinyl ketone. Of these, the hydrocarbon polymerizable monomers are preferred and of these hydrocarbon monomers, the terminal olefin monomers are particularly preferred.

Useful polymers include α-olefin homopolymers and interpolymers, and ethylene/α-olefin copolymers and terpolymers. Specific examples of polyalkenes include polypropylene, polybutene, ethylene-propylene copolymer, ethylene-butene copolymer, propylene-butene copolymer, styrene-isobutylene copolymer, isobutylene-butadiene-1,3 copolymer, propene-isoprene copolymer, isobutylene-chloroprene copolymer, isobutylene- (para-methyl) styrene copolymer, copolymer of hexene-1 with hexadiene-1,3, copolymer of octene-1, copolymer of 3,3-dimethyl-pentene-1 with hexene-1, and terpolymer of isobutylene, styrene and piperylene. More specific examples of such interpolymers include copolymer of 95% (by weight) of isobutylene with 5% (by weight) of styrene; terpolymer of 98% of isobutylene with 1% of piperylene and 1% of chloroprene; terpolymer of 95% of isobutylene with 2% of butene-1 and 3% of hexene-1; terpolymer of 60% of isobutylene with 20% of pentene-1; and 20% of octene-1; terpolymer of 90% of isobutylene with 2% of cyclohexene and 8% of propylene; and copolymer of 80% of ethylene and 20% of propylene.

A useful source of polyalkenes are the polybutylenes obtained by polymerization of $C_4$ refinery streams having a butene content of about 35 to about 75% by weight and an isobutylene content of about 30 to about 60% by weight in the presence of a Lewis acid catalyst such as aluminum trichloride or boron trifluoride.

It must be noted, however, that polyisobutylene contains quarternary carbon atoms in the polymer chain. Consequently, if the alkylating catalyst is highly acidic (e.g., a heteropoly acid catalyst), highly stable tertiary carbocations may form, thereby either cracking the polymer chain, migrating inward from the terminus of the chain and thereby shifting the location of the double bond, or some combination of both. Depending upon the strength of the acid and the residence time of the reaction, one may expect the Mn of the polyisobutyl chains of the alkylated hydroxyaromatics to be substantially less than the Mn of the polyisobutylene starting material and to find dimers, trimers and oligomers mixed in with the reaction product.

The degradation of quarternary carbon-containing polymer alkylating agents in the presence of strong acid catalyst is one reason why α-olefin homopolymers and interpolymers as well as ethylene/α-olefin copolymers and terpolymers are preferred.

Also useful are high molecular weight poly-n-butenes. Reference is made to commonly assigned copending U.S. Ser. No. 992,871, filed Dec. 17, 1992 entitled, "Amorphous Olefin Polymers, Copolymers, Methods of Preparation and Derivatives Thereof".

A preferred source of monomer for making poly-n-butenes is petroleum feedstreams such as Raffinate-2. These feedstocks are disclosed in the art such as in U.S. Pat. No. 4,952,739.

Preparing polyalkenes as described above which meet the various criteria for Mn and Mw/Mn is within the skill of the art and does not comprise part of the present invention.

Ethylene/α-olefin Copolymer

The most preferred polymers suitable for use as alkylating agents are polymers of ethylene and at least one α-olefin, the α-olefin typically having the formula $H_2C=CHR^4$ wherein $R^4$ is straight chain or branched chain alkyl radical comprising 1 to 18 carbon atoms and wherein the polymer contains a high degree of terminal ethenylidene unsaturation. Preferably $R^4$ in the above formula is alkyl of from 1 to 8 carbon atoms and more preferably is alkyl of from 1 to 2 carbon atoms. Therefore, useful comonomers with ethylene in this invention include propylene, butene-1, hexene-1, octene-1, 4-methylpentene-1, decene-1, dodecene-1, tridecene-1, tetradecene-1, pentadecene-1, hexadecene-1, heptadecene-1, octadecene-1, nonadecene-1 and mixtures thereof (e.g., mixtures of propylene and butene-1, and the like). Preferred polymers are copolymers of ethylene and propylene and ethylene and butene-1.

The ethylene content of the polymers employed is preferably in the range of between about 20 and about 80%, and more preferably between about 30 and about 70% by mole. When butene-1 is employed as comonomer with ethylene, the ethylene content of such copolymer is most preferably between about 20 and about 45% by weight, although higher or lower ethylene contents may be present.

Preferred ethylene/butene-1 copolymers are disclosed in commonly assigned U.S. Ser. No. 992,192, filed Dec. 17, 1992, titled POLYMERS DERIVED FROM ETHYLENE AND 1-BUTENE FOR USE IN THE PREPARATION OF LUBRICANT DISPERSANT ADDITIVES, wherein is disclosed an oil soluble copolymer comprising from 1 to about 50 weight percent monomer units derived from ethylene and from about 99 to about 50 weight percent monomer units derived from butene-1, based on the total polymer weight, and having a number average molecular weight between about 1,500 and 7,500, ethylvinylidene groups terminating at least about 30 percent of all copolymer chains, and an absence of aggregation in solution with mineral oil as determined by having an $S_f$ value(light-scattering factor) of about zero.

A preferred method for making ethylene/α-olefin copolymer is described in commonly assigned U.S. Ser. No. 992,690, filed Dec. 17, 1992, titled DILUTE PROCESS FOR THE POLYMERIZATION OF ETHYLENE/α-OLEFIN COPOLYMER USING METALLOCENE CATALYST SYSTEMS, wherein there is described a process for continuously producing copolymer comprising monomer units derived from ethylene and α-olefin in the presence of a metallocene catalyst system and in a reaction zone containing liquid phase which comprises (A) continuously providing a dilute liquefied α-olefin feed stream comprising at least one α-olefin reactant and diluent admixed therewith wherein the amount of diluent in said feed stream is at least 30% weight percent thereof; (B) providing a feed stream comprising ethylene in liquid, vapor, or liquid/-vapor form; (C) admixing, the feed streams of steps (A) and (B) in amounts sufficient to provide a reactant feed stream having an α-olefin/ethylene weight ratio effective to yield a copolymer containing between about 5 to about 70 weight percent monomer units derived from ethylene; (D) continuously introducing reactant feed stream derived in accordance with step (C) and metallocene catalyst system into the liquid phase of the reaction zone in a manner and under conditions sufficient to: (i) polymerize the ethylene and α-olefin to polymer product having a number average molecular weight of not greater than about 15,000 (ii), obtain an α-olefin conversion of at least 30%, and (iii) obtain an ethylene conversion of at least 70%; and (E) continuously withdrawing copolymer product from the reactor.

The ethylene/α-olefin polymers generally possess a number average molecular weight as recited. Preferred ranges of molecular weights of polymer for use as precursors for dispersants are from about 500 to about 10,000, preferably of from about 1,000 to about 8,000, most preferably of from about 2,000 to about 6,000. The number average molecular weight for such polymers can be determined by several known techniques. A convenient method for such determination is by size exclusion chromatography (also known as gel permeation chromatography, or GPC) which additionally provides molecular weight distribution information, see W. W. Yau, J. J. Kirkland and D. D. Bly, "Modern Size Exclusion Liquid Chromatography", John Wiley and Sons, New York, 1979. Such polymers generally possess an intrinsic viscosity (as measured in tetralin at 135° C.) of between about 0.025 and about 0.6 dl/g, preferably of between about 0.05 and about 0.5 dl/g, most preferably of between about 0.075 and about 0.4 dl/g. These polymers preferably exhibit a degree of crystallinity such that, when functionalized, they are oil soluble.

The preferred ethylene/α-olefin polymers are further characterized in that the polymer chains possess as much terminal ethenylidene- and ethenyl-type unsaturation as possible. Thus, one end of such polymers will be of the formula POLY'—C(R")=CH$_2$ wherein R" is C$_1$ to C$_{18}$ alkyl, preferably C$_1$ to C$_8$ alkyl, and more preferably C$_1$ to C$_2$ alkyl, (e.g., methyl or ethyl) and wherein POLY' represents the polymer chain; and a minor amount of the polymer chains may contain terminal ethenyl (i.e., "vinyl") unsaturation, i.e., POLY'—CH=CH$_2$. The chain length of the R" alkyl group will vary depending on the comonomer(s) selected for use in the polymerization. A portion of the polymers can contain internal monounsaturation, e.g., POLY'—CH=CH(R"), wherein R" is as defined above.

Preferred ethylene/α-olefin polymer comprises polymer chains, at least about 30% of which possess terminal ethenylidene unsaturation. Preferably at least about 50%, more preferably at least about 60%, and most preferably at least about 75% (e.g., 75 to 98%), of such polymer chains exhibit terminal ethenylidene unsaturation. The percentage of polymer chains exhibiting terminal ethenylidene unsaturation may be determined by FTIR spectroscopic analysis, titration, HNMR, or C$_{13}$NMR. Such polymers also generally exhibit a minor percentage of highly desirable ethenyl (vinyl) unsaturation, which may be substituted for ethenylidene unsaturation in arriving at the percentages disclosed above. Hence, for example, a combined percentage of 30% ethenylidene and ethenyl unsaturation will more than adequately substitute for 30% ethenylidene alone—and should even prove superior by virtue of the higher reactivity of terminal ethenyl in comparison to that of terminal ethenylidene.

The ethylene/α-olefin polymer and the compositions employed in this invention may be prepared as described in U.S. Pat. No. 4,668,834, in European Patent Publications 128,046 and 129,368, and in copending Ser. No. 728,111, filed Apr. 29, 1985, and copending Ser. No. 93,460, filed Sep. 10, 1987.

The polymers can be prepared by polymerizing monomer mixtures comprising ethylene in combination with other monomers such as α-olefins having from 3 to 20 carbon atoms (and preferably from 3 to 4 carbon atoms, i.e., propylene, butene-1, and mixtures thereof) in the presence of a metallocene catalyst system comprising at least one metallocene (e.g., a cyclopentadienyl-transition metal compound) and an activator, e.g., alumoxane compound. The comonomer content can be controlled through the selection of the metallocene catalyst component and by controlling the partial pressure of the various monomers.

The polymer for use in the present invention can include block and tapered copolymers derived from monomers comprising at least one conjugated diene with at least one monovinyl aromatic monomer, preferably styrene. Useful polymers include polymers of the type disclosed in U.S. Pat. Nos. 4,073,737 and 3,795,615.

Such polymers should not be completely hydrogenated so that the polymeric composition contains terminal olefinic double bonds, preferably at least one bond per molecule. Useful polymers include an oil soluble copolymer of the following general formula:

$$(A)_x(B)_y \qquad (4)$$

wherein:

A is a conjugated diene of the formula:

wherein R$^9$ is a H or C$_1$ to C$_8$ alkyl group, preferably H or CH$_3$ (i.e., isoprene) and present in mole % proportion as indicated by x which may vary from 45 to 99 mole %;

B is a C$_8$ to C$_{20}$ monovinyl aromatic compound and/or aromatic substituted diene and present in weight % proportion as indicated by y which may vary from 1 to 55 mole %; typically from 25 to 30 mole %, and preferably from 5 to 40 mole %. The lattermost range representing where the most useful composite properties of oxidative stability and −18° C. viscosity of the lubricating oil blend is realized.

Block copolymers as used herein includes "multiple block copolymers" which term denotes copolymers consisting of two or more of the single block copolymers described above, which are bound to each other. A multiple block copolymer may, for example, be prepared by first copolymerizing to completion a mixture of butadiene and isoprene, thereafter polymerizing styrene onto said copolymer and subsequently sequentially copolymerizing a mixture of butadiene and isoprene followed by said styrene onto the "living" block copolymer. For purposes of this disclosure, a "living" copolymer is one which remains stable over an extended period of time during which additional monomers can be added to it.

Multiple block copolymers can also be obtained in other ways such as by coupling of two or more "living" block copolymer molecules. This can be achieved by addition of a compound which reacts with two or more "living" single block copolymer molecules. Examples of this type of compound include compounds containing two or more ester groups, 5 compounds with more than one active halogen atom, e.g., di- and tri-chloromethyl-benzene, phosgene, dichlorosilane, carbon tetrachloride, dimethyldichlorosilane, 1,2-dichloroethane, 1,2-dibromo-methane, and the like. Another possible method for preparing multiple block copolymers consists in the preparation of single block copolymer containing a reactive group in the molecule (e.g., a carboxyl group, which is, for example, obtained by bringing the polymerization of a single copolymer to an end by addition of carbon dioxide) and coupling of two or more of the molecules, e.g., by esterifying them with a di- or polyvalent alcohol. Multiple block copolymers have the further advantage that they can be tailored to provide the most useful additive properties while masking one or more undesirable properties inherent in any polymer block.

The present invention can also include star polymers as disclosed in patents such as U.S. Pat. Nos. 5,070,131; 4,108,945 and 3,711,406 as well as 5,049,294. Particularly useful star polymers are disclosed in U.S. Pat. No. 5,070,131.

The Alkylation of the Dihydroxyaromatics

The alkylation of the dihydroxyaromatic compounds may be carried out by methods known in the art, as by the use of acid catalysts such as sulfuric acid, boron triflouride and aluminum chloride such as described in U.S. Pat. No. 4,735,582, and EP Publication 440,507 A2. Such catalyst are often referred to as "homogeneous" catalyst because they either dissolve into the reaction mixture or are liquid at reaction temperature and pressure.

Preferred alkylation catalysts are the so called "heterogeneous" catalysts. Such catalysts remain solid during the alkylation and are therefore easy to separate from the product mixture. Suitable heterogeneous catalysts include zeolites, as are disclosed in U.S. Pat. Nos. 4,283,573 4,731,497 and 4,954,663; mole sieves and exchange resins such as are described in U.S. Pat. Nos. 4,323,714 and 4,849,569 and EP Publication 387,080; clays, layered materials and composites thereof such as are described in UK Patent Application 2,120,953 and EP Application 400,857; and hydrated heteropoly acids and excess water as is described in U.S. Pat. No. 4,912,264. Supported heteropoly acids such as are described in U.S. Pat. No. 3,346,657 are also suitable. Amberlyst 15 is also a preferred heterogeneous catalyst.

A particularly preferred catalyst is a dehydrated heteropoly catalyst as described in Gutierrez et al., POLYMER ALKYLATION OF HYDROXYAROMATIC COMPOUNDS, filed Jun. 2, 1993, U.S. Ser. No. 070,572, wherein there is disclosed a process for alkylating hydroxyaromatic compounds comprising contacting, in the liquid phase, a hydroxyaromatic compound, a polymer alkylating agent of at least about 500 average number molecular weight and having at least one reactive carbon-carbon double bond unsaturation, and a heteropoly catalyst having substantially no waters of crystallization per heteropolyanion therein. Such catalysts include phosphomolybdic acid, silicomolybdic acid, arsenomolybdic acid, telluromolybdic acid, aluminomolybdic acid, silicotungstic acid, phosphotungstic acid, borotungstic acid, titanotungstic acid, stannotungstic acid, and salts thereof. The catalyst is prepared for the reaction by driving water of hydration and crystallization out of the catalyst, either before or during the alkylation. Advantages include the ability to easily alkylate hydroxyaromatics with polymer alkylating agents having molecular weights well over 1000. Reaction temperatures vary from about 20° C. to 250° C., but will be conducted above the boiling point of water in cases where water needs to be driven out of the catalyst during alkylation.

Alkylation of dihydroxyaromatic compounds in the presence of Amberlyst 15 are typically carried out at temperatures from 10° to 150° C., generally 20° to 120° C., preferably 80° to 110° C. for reaction times of from 0.5 to 24 hours, generally 1 to 12 hours, preferably 2 to 6 hours.

The Amines

The amines useful in the present invention are polyamines having at least one primary or secondary amine group.

Preferred polyamines are aliphatic saturated amines, including those of the following structural formulas:

(III)

(IV)

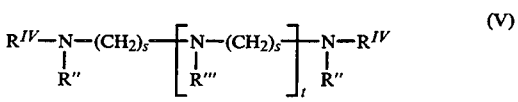

(V)

wherein n is an integer of at least 1 and $R'$, $R''$, $R'''$, and $R^{IV}$ are independently selected from the group consisting of hydrogen; $C_1$ to $C_{25}$ straight or branched chain alkyl radicals; $C_1$ to $C_{12}$ alkoxy $C_2$ to $C_6$ alkylene radicals; $C_2$ to $C_{12}$ hydroxy amino alkylene radicals; and $C_1$ to $C_{12}$ alkylamino $C_2$ to $C_6$ alkylene radicals; and wherein $R''$ and $R'''$ can additionally comprise a moiety of the formula:

(VI)

wherein $R'$ is as defined above, and wherein each s and s' can be the same or a different number of from 2 to 6, preferably 2 to 4; and t and t' can be the same or different and are each numbers of typically from 0 to 10, preferably about 2 to 7, most preferably about 3 to 7, with the proviso that $t+t'$ is not greater than 10. To assure a facile reaction it is preferred that $R'$, $R''$, $R'''$, $R^{IV}$, s, s', t, and t' be selected in a manner sufficient to provide the compounds of formulas IV and V with at least one primary amino group. This can be achieved by selecting at least two of said $R'$, $R''$, or $R^{IV}$ groups in formula IV to be hydrogen, selecting both $R'$ and $R^{IV}$ in formula V to be hydrogen, or by selecting t in formula V to be at least one when the moiety of formula VI possesses a primary amino group.

Non-limiting examples of suitable amine compounds include: 1,2-diaminoethane; 1,3-diaminopropane; 1,4-diaminobutane; 1,6-diaminohexane; polyethylene amines such as diethylenetriamine (DETA); triethylene tetramine; tetraethylene pentamine; polypropylene amines such as 1,2-propylene diamine; di-(1,2-propylene) triamine; di-(1,3-propylene) triamine; N,N-dimethyl-1,3-propanediamine (also known as N,N-dimethylaminopropylamine, or DMAPA); N,N-di-(2-aminoethyl) ethylene diamine; N, N-di-(2-hydroxyethyl)-1,3-propylene diamine; N-dodecyl-1,3-propane diamine; and mixtures thereof.

Other useful amine compounds include: alicyclic diamines such as 1,4-di-(aminoethyl)cyclohexane, and N-aminoalkyl piperazines of the general formula:

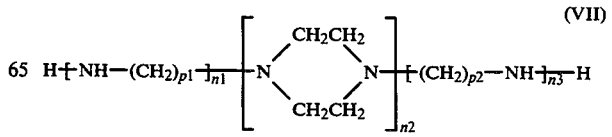

(VII)

wherein p1 and p2 are the same or different and are each integers of from 1 to 4, and n1, n2, and n3 are the same or different and are each integers of from 1 to 3.

Commercial mixtures of amine compounds may advantageously be used. For example, one process for preparing alkylene amines involves the reaction of an alkylene dihalide (such as ethylene dichloride or propylene dichloride) with ammonia, which results in a complex mixture of alkylene amines wherein pairs of nitrogens are joined by alkylene groups, forming such compounds as diethylene triamine, triethylenetetramine, tetraethylene pentamine, and corresponding piperazines.

Particularly preferred amines include low cost poly(ethyleneamine) compounds, often referred to as PAM, averaging about 5 to 7 nitrogen atoms per molecule. These are commercially available under trade names such as "Polyamine H", "Polyamine 400", "Dow Polyamine E-100", among others.

Also useful are polyoxyalkylene polyamines, such as those of the formula:

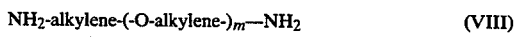

NH$_2$-alkylene-(-O-alkylene-)$_m$—NH$_2$      (VIII)

where m has a value of about 3 to about 70 and preferably about 10 to about 35; and

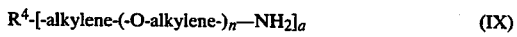

R$^4$-[-alkylene-(-O-alkylene-)$_n$—NH$_2$]$_a$      (IX)

where n has a value of about 1 to 40, with the provision that the sum of all the n's is from about 3 to about 70, and preferably from about 6 to about 35, and R$^4$ is a substituted saturated hydrocarbon radical of up to 10 carbon atoms, wherein the number of substituents on the R$^4$ group is from 3 to 6, and "a" is a number from 3 to 6 representing the number of substituents on R$^4$. The alkylene groups in either formula VIII or IX may be straight or branched chains containing about 2 to about 7, and preferably about 2 to about 4 carbon atoms.

Particularly preferred polyamine compounds include the polyoxyalkylene polyamines of formulas VIII and IX, and the alkylene polyamines represented by the formula:

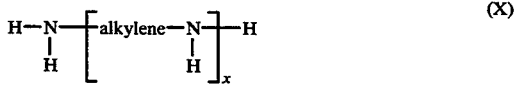

wherein x is an integer of from 1 to about 10, preferably about 2 to about 7, and the alkylene radical is a straight or branched chain alkylene radical having about 2 to about 7, preferably about 2 to about 4 carbon atoms.

Examples of the alkylene polyamines of formula X include methylene amines, ethylene amines, butylene amines, propylene amines, pentylene amines, hexylene amines, heptylene amines octylene amines, other polymethylene amines, the cyclic and higher homologs of these amines such as the piperazines, the amino-alkyl-substituted piperazines, and the like. These amines include, for example, ethylene diamine, diethylene triamine, triethylene tatramine, propylene diamine, di(heptamethylene)triamine, tripropylene tetramine, tetraethylene pentamine, trimethylene diamine, pentaethylene hexamine, di(trimethylene) triamine, 2-heptyl-3-(2-aminopropyl)imidazoline, 4-methylimidazoline, 1, 3-bis-(2-aminopropyl)piperazine, 1,4-bis(2-aminoethyl)piperazine, N,N-dimethylaminopropylamine (DMAPA), N,N'-dioctylethylamine, N-octyl-N'-methylethylene diamine, 2-methyl-1-(2-aminobutyl)piperazine, and the like. Other higher homologs which may be used can be obtained by condensing two or more of the above-mentioned alkylene amines in a known manner.

The ethylene amines which are particularly useful are described, for example, in the Encyclopedia of Chemical Technology under the heading of "Ethylene Amines" (Kirk and Othmer), Volume 5, pp. 898–905; Interscience Publishers, New York (1950). These compounds are prepared by the reaction of an alkylene chloride with ammonia, which results in the production of a complex mixture of alkylene amines, including cyclic condensation products such as piperazines. Mixtures of these amines may also be used for the purposes of this invention.

The polyoxyalkylene polyamines of formulas VIII and IX, preferably polyoxyalkylene diamines and polyoxyalkylene triamines, may possess average molecular weights ranging from about 200 to about 4000 and preferably from about 400 to about 2000. The preferred polyoxyalkylene polyamines include the polyoxyethylene and the polyoxypropylene diamines and the polyoxypropylene triamines having average molecular weights ranging from about 200 to about 2000. The polyoxyalkylene polyamines are commercially available and may be obtained, for example, from the Jefferson Chemical Company, Inc. under the trade names "Jeffamines D-230, D-400, D-1000, D-2000, T-403", etc.

The Amination Reaction Conditions

Without limiting the present invention to a particular theory, it is believed that an alkylated quinone-type (i.e., dicarbonyl) intermediate is created (e.g., an alkylated 1,4-benzoquinone in the case where hydroquinone is used as the dihydroxyaromatic; an alkylated 1,2-benzoquinone in the case of catechol) during the reaction that is then subsequently aminated. It is therefore possible to use alkylated dicarbonyl analogues of the dihydroxyaromatics of the present invention as starting material and aminate them directly in accordance with the methods disclosed herein.

It is preferred that the reaction mixture be exposed to an oxidizing agent such that the alkylated dihydroxyaromatic is oxidized to the corresponding alkylated dicarbonyl intermediate. The dicarbonyl then reacts with the amine. Simple exposure to atmospheric oxygen during the reaction is sufficient for this purpose, though other oxidizing agents may be employed. The alkylation, oxidation, and amination steps may be easily followed by spectroscopic techniques such as infrared or NMR spectroscopy.

Failure to use an oxidizing agent will result in poor yields, since it may be expected that one molecule of reactant will be consumed in order to oxidize another to form one molecule of final product.

The amination of the present invention is preferably performed in an inert solvent, such as a hydrocarbon. Useful hydrocarbons include heptane, cyclohexane, toluene, xylene, mineral oil, and the like.

The alkylated dihydroxyaromatic compound, primary amine, and solvent are mixed and will generally be reacted at a temperature of from 0° to 200° C., preferably 10° to 110° C. (e.g., 20° to 100° C.), for a period of from 0.5 to 168 hours, preferably 1 to 48 (e.g., 1.5 to 12; 2 to 6) hours.

Depending upon such factors as the reactants chosen and the nitrogen content of the final product desired, the amines of the present invention will generally be employed in the amount of from 0.01 mole of amine per mole of dihydoxyaromatic to 10 moles of amine per mole of dihydoxyaromatic, preferably 0.1 to 5 moles of amine per mole of dihydroxyaromatic (e.g., 0.3 to 2; 0.5 to 1).

Lubricant Compositions

The products prepared by the process of this invention are very suitable for use in lubricating oils. The lubricating oils can be any animal, vegetable or mineral oil, for example petroleum oil to SAE 30, 40 or 50 lubricating oil grades, castor oil, fish oils or oxidized mineral oils.

Alternatively the lubricating oil can be a synthetic ester lubricating oil and these include diesters such as di-octyl adipate, di-octyl sebacate, didecyl azelate, tridecyl adipate, didecyl succinate, didecyl glutarate and mixtures thereof. Alternatively the synthetic ester can be a polyester such as that prepared by reacting polyhydric alcohols such as trimethylolpropane and pentaerythritol with monocarboxylic acids such as butyric acid to give the corresponding tri- and tetra-esters. Also complex esters may be used, such as those formed by esterification reactions between carboxylic acid, a glycol and an alcohol, or monocarboxylic acid.

Base oils suitable for use in preparing the lubricating oil compositions of the present invention include those conventionally employed as crankcase lubricating oils for spark-ignited and compression-ignited internal combustion engines, such as automobile and truck engines, marine and railroad diesel engines, and the like. Advantageous results are also achieved by employing the products of the present invention in base oils conventionally employed in and/or adapted for use as power transmitting fluids such as automatic transmission fluids, tractor fluids, universal tractor fluids and hydraulic fluids, heavy duty hydraulic fluids, power steering fluids and the like. Gear lubricants, industrial oils, pump oils and other lubricating oil compositions can also benefit from the incorporation therein of the products of the present invention.

The amount of product alkylated with dispersant-range molecular weight polymer alkylating agent added to a lubricating oil is typically a minor proportion and will generally be blended in proportions of from 0.01% to 30% by weight of lubricating oil (e.g., 0.01% to 20% by weight), preferably between 0.1% and 8% by weight (e.g., 0.1% to 5% by weight).

The amount of product alkylated with viscosity-modifier-range molecular weight polymer alkylating agent added to a lubricating oil is typically a minor proportion and will generally be blended in proportions of from 0.01% to 20% by weight of lubricating oil (e.g., 0.01% to 12% by weight), preferably between 0.01% and 6% by weight (e.g., 0.01% to 4% by weight).

The products of the present invention may be borated by means known in the art.

Fuel Compositions

The products of this invention are suitable for use in normally liquid petroleum fuels such as middle distillates boiling from about 65° C. to 430° C., including kerosene, diesel fuels, home heating fuel oil, and jet fuels.

The amount of product alkylated with dispersant-range molecular weight polymer alkylating agent added to a fuel oil is typically a minor proportion and will generally be blended in proportions of from 0.001% to 0.5% by weight of fuel oil (e.g., 0,001% to 0.3% by weight), preferably between 0.001% and 0.15% by weight (e.g., 0.005% to 0.1% by weight).

The final fuel and lubricating oil compositions may if desired contain other additives known in the additive art, e.g., other viscosity index improvers and dispersants, detergents, antioxidants, corrosion inhibitors, pour point depressants, antiwear agents, friction modifiers, and the like.

EXAMPLES

Examples 1 to 5: Alkylation of Hydroquinone

In each of Examples 1 through 5, a quantity of hydroquinone (MW=110) was dissolved in a quantity of either heptane or toluene and charged to a 250 ml. round-bottom flask. A quantity of Amberlite-15 (a strongly acidic resin comprising divinylbenzene-cross-linked polystyrene, to which sulfonic groups are attached) was added, followed by the addition of a quantity of an ethylene/propylene copolymer ("EP polymer") having a number average molecular weight of 870 and terminal unsaturation. Each reaction mixture was then heated for a number of hours and then filtered, followed by the removal of the solvent under vacuum.

IR spectra of the products revealed new peaks appearing at 3600 and 1400 cm$^{-1}$ (thereby indicating a change in the nature of the hydroxyl groups on the aromatic ring that would indicate the presence of a substituent thereon) and complete disappearance of the double bond peaks of the EP polymer at 3065, 1645 and 885 cm$^{-1}$ (thereby indicating the loss of the polymer unsaturation). This indicates that the dihydroxyaromatic was successfully alkylated. The alkylation procedures are shown in Table I as follows:

TABLE I

| Ex. No. | Hydro-quinone g. | Sol-vent | Sol-vent ml. | Amber-lite g. | EP g. | RX Temp °C. | RX Time hrs. |
|---|---|---|---|---|---|---|---|
| 1 | 6.32 | Hep | 50 | 12.5 | 25 | 98 | 6.0 |
| 2 | 30.00 | Tol | 50 | 15.0 | 50 | 90 | 2.0 |
| 3 | 3.16 | Hep | 30 | 15.0 | 50 | 90 | 2.5 |
| 4 | 6.32 | Hep | 30 | 15.0 | 50 | 90 | 2.5 |
| 5 | 12.64 | Hep | 30 | 15.0 | 50 | 90 | 2.5 |

Example 6: Alkylation of Catechol

Into a 250 ml. round-bottom flask were charged 6.32 g. (0.0575 moles) of Catechol (MW=110) and 50 ml of toluene. To this was added 10 g. of Amberlite-15 and the mixture was heated to 90° C. Added to this was 50 g. of an EP polymer (MW=870) and the solution was maintained at 90° C. for another 2 hours. The reaction mixture was then filtered, the filtrate evaporated, and the resultant product redissolved in heptane. The heptane solution was itself filtered and the filtrate evaporated under vacuum to obtain the product.

Examples 7 through 12: Amination of Alkylated Hydroquinone with PAM

In each of examples 7 through 12, 2 g. of the EP-hydroquinone produced in Example 5 were dissolved in 50 ml heptane. To this was added a quantity of either PAM (polyethyleneamine having an average of 5 to 7 nitrogen atoms per molecule),DETA (diethylenetriamine, MW=103), or DMAPA (N,N-dimethylaminopropylamine, MW=103). Each solution was stirred at room temperature for 24 hours and then diluted with 50 ml of heptane and filtered. The solvent was removed by nitrogen stripping followed by evaporation under high vacuum. The products were analyzed for nitrogen content. The results are summarized in Table II as follows:

TABLE II

| Ex. No. | Amine | Amine g. | Nitrogen Content wt. % |
|---|---|---|---|
| 7 | PAM | 0.150 | 2.18 |
| 8 | PAM | 0.300 | 3.27 |
| 9 | DETA | 0.103 | 1.58 |
| 10 | DETA | 0.206 | 2.65 |
| 11 | DMAPA | 0.103 | 0.33 |
| 12 | DMAPA | 0.206 | 0.40 |

Example 13: Amination of Alkylated Catechol with DMAPA 4.32 g. of the product of Example 6 were dissolved in 50 ml of heptane. To this mixture was added 0.9 g. of DMAPA and the solution was refluxed for 6 hours at 98° C. Afterwards, the heptane was removed by nitrogen stripping followed by evaporation under high vacuum.

The nitrogen content of the product was found to be 1.20 wt. %.

Dispersancy Performance

The performance of the products of Examples 7 through 13 were tested for sludge inhibition and varnish inhibition as described herein.

The test for sludge inhibition is referred to as the SIB test. The SIB test has been found to be excellent for assessing the dispersing power of lubricating oil dispersant additives.

The medium chosen for the SIB test is a crankcase mineral lubricating oil composition having an original viscosity of about 325 SUS at 38° C. that has been used in a taxicab driven for short trips only, thereby resulting in the buildup of high concentrations of sludge precursors. The oil used in the taxi contains only a refined base mineral lubricating oil, a viscosity index improver, a pour point depressant, and a zinc dialkyl-dithiophosphate anti-wear additive. The oil contains no sludge dispersant. A quantity of such used oil is acquired by draining and refilling the taxicab crankcase at 1,000 to 2,000 mile intervals.

The SIB test is conducted by first taking the aforesaid used crankcase oil from the taxi and centrifuging the milky brown fluid for 1 hour at about 39,000 gravities (gs). The resultant clear bright red supernatant oil is decanted from the sludge particles. The sludge has been removed from this supernatant but it still contains sludge precursors, which upon heating will convert to additional sludge.

A small amount of each dispersant being tested is then added to a quantity of the supernatant and heated at 135° C. for 16 hours in the presence of air. A sample of the supernatant without any dispersant added is used as the standard, while a sample having a well known commercially available dispersant blended therein is often used as a reference. After heating, the samples are cooled to room temperature and centrifuged at about 39,000 gs. Any sludge removed by this step is separated by decanting the resulting supernatant and washing the precipitate with heptane, followed by additional centrifugation. The sludge precipitate is then dried and weighed.

The SIB score is determined by comparison with the standard (the sample having no dispersant). The weight of the sludge precipitate removed from the standard is normalized to 10. The amount of sludge precipitated from the other samples are scored by weight. Hence, if the precipitate from the standard were found to have weighed 22 grams, for example, and the precipitate from a particular dispersant sample weighed 11 grams, then the dispersant sample scores 5 after normalization of the standard to 10. As can be seen, the lower the SIB score, the better the sludge deposit inhibition qualities of the dispersant.

An SIB score greater than 10 indicates that the additive being tested demonstrates worse sludge deposit inhibition qualities than no additive at all. Such an additive would be classified as a flocculant.

The VIB test is used to determine varnish inhibition. Here, small quantities of dispersant are added to a supernatant oil having sludge precursors, just as described above with respect to the SIB test. Each sample is heat soaked overnight at about 140° C. and then centrifuged to remove the sludge precipitate. The precipitate is removed and the supernatant is then subjected to heat cycling of from room temperature to 150° C. at a frequency of about 2 cycles per minute over a 3.5 hour period. During the heating phase of each cycle, a gas comprising 0.7% $SO_2$ by volume, 1.4% NO by volume, and the remainder air, is bubbled through each test sample. These cycling periods may be repeated as necessary.

After heat cycling, the flasks in which the samples are contained are visually examined for varnish deposits. The samples are subjectively rated against the standard on a scale of 1 to 11, wherein a score of 1 indicates no varnish deposits at all and the standard (having no dispersant) is given a rating of 11. Hence, the lower the score, the better the varnish inhibition qualities of the dispersant.

A VIB score greater than 11 indicates that the varnish inhibition qualities of the tested additive are worse than no additive at all. The reference used in the table below was a PIBSA-PAM 5 dispersant wherein the polyisobutylene moiety had a number average molecular weight Of about 950, the number of succinimide moieties to each polyisobutylene chain was about 1.18, and the nitrogen content of each molecule averaged 1.59% by weight. The reference is considered representative of dispersants currently in commercial use.

The results of SIB and VIB tests on the products of Examples 7 through 13 were as follows:

TABLE III

| Example No. | SIB mg | VIB rating |
|---|---|---|
| 7 | 7.1 | 4 |
| 8 | 8.5 | 4 |
| 9 | 8.0 | 5+** |
| 10 | 8.5 | 4 |
| 11 | 5.85 | 5—** |
| 12 | 5.75 | 6 |
| 13 | 1.59 | 4 |
| Reference* | 4.20 ± 0.68 | 7 ± 0 |

TABLE III-continued

| Example No. | SIB mg | VIB rating |
|---|---|---|
| Standard | 10.00 | 11.00 |

*the catechol- and hydroquinone-derived dispersants were evaluated in two separate sets of SIB and VIB tests using two separate samples of supernatant crankcase oil. Hence, the reference score for each test is not exactly the same. Here, the two scores from the SIB tests and the two scores from the VIB tests were averaged.
**A "+" indicates a slightly higher value, a "−" slightly lower. No attempt at greater accuracy is made since the evaluation is necessarily subjective.

As can be seen, the catechol derived dispersant (Example 13) displayed the most impressive sludge-reducing properties and significant varnish reducing properties over the reference. Hydroquinone-derived dispersants (Examples 7 to 12) showed improved varnish reduction over the reference.

What is claimed is:

1. A process for the production of fuel and lubricant additives, said process comprising:
   providing an alkylated dihydroxyaromatic compound having been alkylated with a polymer alkylating agent;
   aminating said alkylated dihydroxyaromatic compound with at least one amine under conditions effective in oxidizing the hydroxyl groups of said alkylated dihydroxyaromatic compound to carbonyl groups.

2. The process of claim 1 wherein said dihydroxyaromatic compound is catechol.

3. The process of claim 1 wherein said dihydroxyaromatic compound is hydroquinone.

4. The process of claim 1 wherein said amine is at least one selected from the group consisting of amines represented by the following structural formulas:

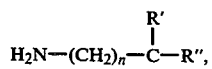

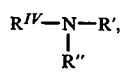

and

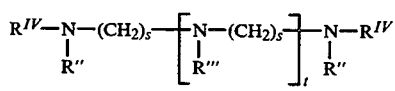

wherein n is an integer of at least 1 and R', R", R'", and R$^{IV}$ are independently selected from the group consisting of hydrogen; C$_1$ to C$_{25}$ straight or branched chain alkyl radicals; C$_1$ to C$_{12}$ alkoxy C$_2$ to C$_6$ alkylene radicals; C$_2$ to C$_{12}$ hydroxy amino alkylene radicals; and C$_1$ to C$_{12}$ alkylamino C$_2$ to C$_6$ alkylene radicals.

5. The process of claim 4 wherein R" and R'" further comprise a moiety of the formula:

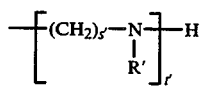

wherein each s and s' is the same or a different number of from 2 to 6,; and t and t' is the same or different and are each numbers of from 0 to 10, with the proviso that t+t' is not greater than 10.

6. The process of claim 1 wherein said amine is polyethyleneamine.

7. The process of claim 1 wherein said amine is diethylenetriamine.

8. The process of claim 1 wherein said amine is N,N-dimethylaminopropylamine.

9. The process of claim 1 wherein said polymer alkylating agent is an unsaturated ethylene/α-olefin copolymer.

10. The process of claim 9 wherein said α-olefin comprises four carbon atoms.

11. The process of claim 1 wherein said polymer alkylating agent is an unsaturated propylene/butene-1 copolymer.

12. The process of claim 1 wherein said polymer alkylating agent is an unsaturated homopolymer of an olefin monomer, said monomer having four carbon atoms.

13. The process of any of claims 9 through 12 wherein said polymer alkylating agent comprises at least about 30% combined terminal ethenylidene and ethenyl unsaturation.

14. The process of any of claims 9 through 12 wherein said polymer alkylating agent has a number average molecular weight of about 250 to about 20,000.

15. The product formed by the process of any of claims 1 through 12.

16. An oleaginous composition comprising a major amount of a lubricating oil and a minor amount of the product of claim 15.

17. An oleaginous composition comprising a major amount of a fuel and a minor amount of the product of claim 15.

18. A substance useful as a fuel or lubricant additive having the chemical formula:

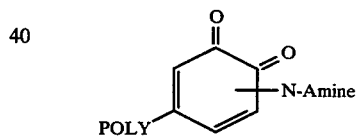

wherein POLY is a polymeric hydrocarbyl and N-Amine is an amine bound to the ring structure via a nitrogen atom.

19. A substance useful as a fuel or lubricant additive having the chemical formula:

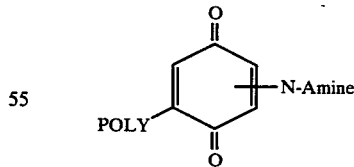

wherein POLY is a polymeric hydrocarbyl and N-Amine is an amine bound to the ring structure via a nitrogen atom.

20. A lubricant composition comprising:
   lubricating oil; and
   at least one of the substances of claims 18 and 19.

* * * * *